United States Patent
Way et al.

(10) Patent No.: US 7,776,972 B2
(45) Date of Patent: Aug. 17, 2010

(54) PHOSPHINE-BASED POLYMERS AND POLY(LACTIC ACID) MATERIAL COMPRISING THE SAME

(75) Inventors: Tun-Fun Way, Hsinchu (TW); Kelly Teng, Taipei (TW); Jiun-Jy Chen, Toufen Township (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 12/463,096

(22) Filed: May 8, 2009

(65) Prior Publication Data

US 2010/0144979 A1 Jun. 10, 2010

(30) Foreign Application Priority Data

Dec. 4, 2008 (TW) .............................. 97147085 A

(51) Int. Cl.
*C08G 63/08* (2006.01)
(52) U.S. Cl. .................. 525/450; 525/418; 525/538; 528/271; 528/361; 528/354; 528/398; 528/400; 558/179; 558/180
(58) Field of Classification Search ................ 525/418, 525/439, 450, 538; 528/271, 354, 361, 398, 528/400; 558/179, 180
See application file for complete search history.

(56) References Cited

OTHER PUBLICATIONS

Yang, X.Z.; Wang, Y.C>; Tang, L.Y.; Xia, H.; Wang, J.; Journal of Polymer Science: Part A: Polymer Chemistry, 2008 (46), p. 6425-6434.*
Kobayashi, S.; Hashimoto, T.; Saegusa, T.; Macromolecules 1980 (13), p. 1650-1654.*
Saegusa, T.; Miyamoto, M.; Kimura, Y.; Macromolecules, 1981 (14), p. 115-117.*

Hideto Tsuji; "Poly(lactide) Stereocomplexes: Formation, Structure, Properties, Degradation, and Applications"; Macromolecular Journals; 2007; pp. 1299.
Bhuvanesh Gupta et al.; "Poly(lactic acid) fiber: An overview"; ScienceDirect; Elsevier; 2007; pp. 455-482.
John A. Cicero et al.; "Phosphate stabilization effects on two-step melt-spun fibers of polylactide"; Polymer Degradation and Stability; Elsevier; 2002; pp. 95-105.
Xiaoyan Yuan et al.; "Characterization of Poly(L-lactic acid) Fibers Produced by Melt Spinning"; Journal of Applied Polymer Science; 2001; vol. 81; pp. 251-260.

* cited by examiner

*Primary Examiner*—David Wu
*Assistant Examiner*—Robert Jones, Jr.
(74) *Attorney, Agent, or Firm*—Lowe Hauptman Ham & Berner, LLP

(57) ABSTRACT

A phosphine-based polymer having Formula (I) is provided.

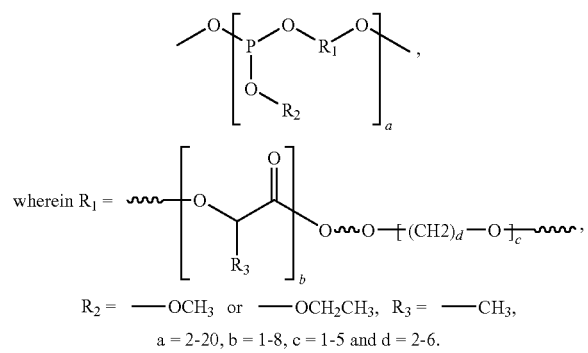

wherein $R_1$ = [structure shown],
$R_2$ = —$OCH_3$ or —$OCH_2CH_3$, $R_3$ = —$CH_3$,
a = 2-20, b = 1-8, c = 1-5 and d = 2-6.

The invention also provides a poly(lactic acid) material including poly(lactic acid) and the disclosed phosphine-based polymer, wherein the phosphine-based polymer has a weight ratio of 0.05-10 parts by weight, based on 100 parts by weight of the poly(lactic acid).

5 Claims, No Drawings

PHOSPHINE-BASED POLYMERS AND POLY(LACTIC ACID) MATERIAL COMPRISING THE SAME

CROSS REFERENCE TO RELATED APPLICATIONS

This Application claims priority of Taiwan Patent Application No. 97147085, filed on Dec. 4, 2008, the entirety of which is incorporated by reference herein.

BACKGROUND OF THE INVENTION

1. Field of the Invention

The invention relates to a polymer, and more particularly to a phosphine-based polymer and a poly(lactic acid) material comprising the same.

2. Description of the Related Art

General polymers produced from petrifaction raw materials, for example, PET, nylon, PP and polystyrene have caused serious river and ditch blockage problems, leading to environmental pollution. Thus, displacement of such general polymers with biodegradable materials is desirable. As economies develop and living standards increase in countries like China, India and Eastern Europe, requirement for petroleum and its related products have substantially increased, resulting in rapid exhaustion of the world's petroleum inventory and rising petroleum and its related product prices. Thus, development of a biomass process utilizing natural materials, for example, soybean, corn, cane, rice and barley combined with biotechnology to produce raw materials is desirable.

Most of the products fabricated by the raw materials produced from biomass processes are biodegradable materials. Poly(lactic acid) (PLA) is prepared from a biomass process and its products possess biodegradability. Cargill Corporation has greatly invested in development of PLA. PLA's price is close to nylon and is expected to be equivalent in price to PET in the future. Currently, PLA is used mostly in commercialization of biodegradable materials or biomass materials. PLA has been widely utilized in biomedicine, agriculture, clothing, furniture, ornaments, implements for daily use and packaging materials.

Applications of PLA, however, suffer from some drawbacks, for example, brittleness, easy pyrolysis and deteriorated processability. Compared to conventional polymers, for example, PET, nylon, PE and PP, PLA's molecular weight is violently decreased during a melt process, achieving 35-60% of its molecular weight. That is, its molecular weight (Mw) ratio (Mw(after processing)/Mw(before processing)) is merely 65-40%, as reported by Bhuvanesh Gupta (Prog. Polym. Sci. 32 (2007) 455 review), such that stability and quality of products made thereof are deteriorated. The same aforementioned result also occurs for modification of the processability of textiles, plastics and thin films. Meanwhile, the decrease in molecular weight of PLA copolymers are more serious than that of PLA homopolymers.

BRIEF SUMMARY OF THE INVENTION

One embodiment of the invention provides a phosphine-based polymer having Formula (I):

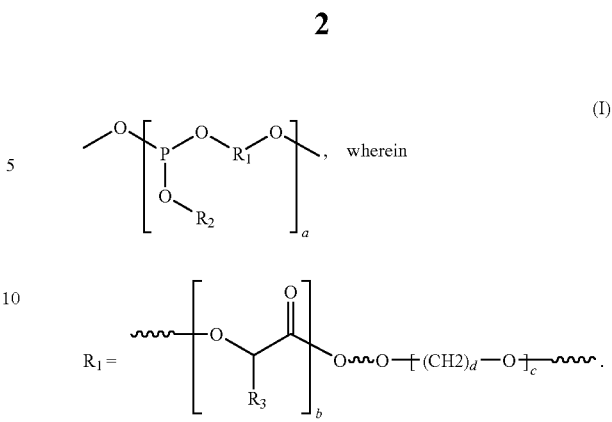

$R_2$=—$OCH_3$ or —$OCH_2CH_3$, $R_3$=—$CH_3$, a=2-20, b=1-8, c=1-5 and d=2-6.

One embodiment of the invention provides a poly(lactic acid) (PLA) material comprising poly(lactic acid) and the disclosed phosphine-based polymer.

When PLA is blended with the phosphine-based polymer and processed, decreasing of the PLA molecular weight is effectively inhibited. The phosphine-based polymer containing the PLA structure is compatible with PLA, reducing compound leakage after blending. Compared to conventional trinonylphenyl phosphine (TNPP) monomers, the phosphine-based polymer has a high boiling point, capable of avoiding evaporation and leakage when being processed. Additionally, compared to TNPP containing nonylphenol, the phosphine-based polymer without nonylphenol acts more like an environmental protection type plasticizer.

In addition to effective improvement of anti-pyrolysis for PLA during processing, the phosphine-based polymer is compatible with PLA and acts more like an environmental protection type plasticizer. Specifically, the molecular weight (Mw) ratio (Mw(after processing)/Mw(before processing)) of the PLA blended with the phosphine-based polymer is not less than 80%. Additionally, the blend of PLA and the phosphine-based polymer with high content, for example, 10 wt % possesses fire retardation (self-extinguishing properties following direct exposure to flames).

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a phosphine-based polymer having Formula (I):

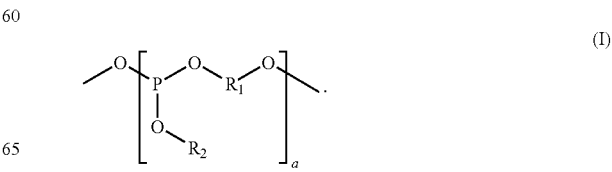

In Formula (I),

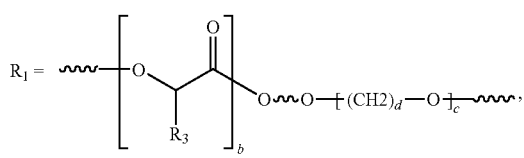

$R_2$=—$OCH_3$ or —$OCH_2CH_3$, $R_3$=—$CH_3$, a=2-20, b=1-8 or 2-5, c=1-5 or 1-2 and d=2-6.

One embodiment of the invention provides a poly(lactic acid) (PLA) material comprising poly(lactic acid) and the disclosed phosphine-based polymer.

The phosphine-based polymer may have a weight ratio of 0.05-10 or 2-3 parts by weight, based on 100 parts by weight of the poly(lactic acid). The poly(lactic acid) material may further comprise inorganic nanoparticles or the like, for example, silicon dioxide, titanium dioxide, zinc dioxide or zirconium dioxide.

The phosphine-based polymer may have a weight ratio of 0.05-10 parts by weight, based on 100 parts by weight of the poly(lactic acid) material. The inorganic nanoparticles may have a weight ratio of 0.05-10 parts by weight, based on 100 parts by weight of the poly(lactic acid) material. The poly (lactic acid) may have a weight ratio of 80-99.9 parts by weight, based on 100 parts by weight of the poly(lactic acid) material.

When PLA is blended with the phosphine-based polymer and processed, decreasing of the PLA molecular weight is effectively inhibited. The phosphine-based polymer containing the PLA structure is compatible with PLA, reducing compound leakage after blending. Compared to conventional trinonylphenyl phosphine (TNPP) monomers, the phosphine-based polymer has a high boiling point, capable of avoiding evaporation and leakage when being processed. Additionally, compared to TNPP containing nonylphenol, the phosphine-based polymer without nonylphenol acts more like an environmental protection type plasticizer.

In addition to effective improvement of anti-pyrolysis of PLA during processing, the phosphine-based polymer is compatible with PLA and acts more like an environmental protection type plasticizer. Specifically, the molecular weight (Mw) ratio (Mw(after processing)/Mw(before processing)) of the PLA blended with the phosphine-based polymer is not less than 80%. Additionally, the blend of PLA and the phosphine-based polymer with high content, for example, 10 wt % possesses fire retardation (self-extinguishing properties following direct exposure to flames).

One embodiment of the invention provides preparing a phosphine-based polymer. A compound having Formula (II) and ($R_2O$)$PCl_2$($R_2$=—$OCH_3$ or —$OCH_2CH_3$) are mixed in a solvent such as chloroform, dichloroethane or tetrahydrofuran (THF) and reacted under a catalyst such as triethylamine, pyridine or diisopropyl ethylamine for 5 hours under a temperature ranging from room temperature to 40° C. to prepare a phosphine-based polymer. The molar ratio between the catalyst and the compound having Formula (II) is 1.5 to 2.5.

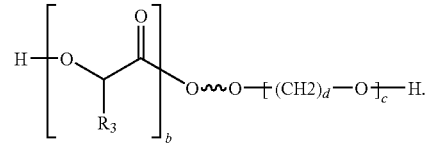

In Formula (II), $R_3$=—$CH_3$, b=1-8, c=1-5 and d=2-6.

EXAMPLE 1

Preparation of the Formula (II) Compound ($R_3$=—$CH_3$, d=6, Monomer is Hexanediol (HDO))

0.75 mole lactic acid methyl ester, 0.125 mole hexanediol (HDO) and 0.3 mole tetrabutyl tin (TBT) were added to a 250 mL reaction bottle and heated to 140° C. under an oil bath to react for 4 hours (sampled each hour). After distilling, a first distillation solution was collected. Next, the first distillation solution was heated to 180° C. to react for 2 hours and sampled. After cooling to 140° C. and distilling, a second distillation solution was collected. The second distillation solution was then heated to 200° C. to react for 2 hours and sampled. After cooling to 140° C. and distilling, a third distillation solution was collected. After reduced-pressure distilling at 130° C., a fourth distillation solution was collected and analyzed. According to $^1$HNMR, the molar ratio between lactate and hexanediol was 4:1.

$^1$HNMR($CDCl_3$, ppm):5.1(lactate); 4.2-4.4(—$OCH_2$—); 1.4-1.5(—$CH_2$); 1.3-1.4(lactate).

EXAMPLE 2

Preparation of the Formula (II) Compound ($R_3$=—$CH_3$, d=2, Monomer is Ethylene Glycol (EG))

0.75 mole lactic acid methyl ester, 0.125 mole ethylene glycol (EG) and 0.3 mole tetrabutyl tin (TBT) were added to a 250 mL reaction bottle and heated to 140° C. under an oil bath to react for 4 hours (sampled each hour). After distilling, a first distillation solution was collected. Next, the first distillation solution was heated to 180° C. to react for 2 hours and sampled. After cooling to 140° C. and distilling, a second distillation solution was collected. The second distillation solution was then heated to 200° C. to react for 2 hours and sampled. After cooling to 140° C. and distilling, a third distillation solution was collected. After reduced-pressure distilling at 130° C., a fourth distillation solution was collected and analyzed.

$^1$HNMR($CDCl_3$, ppm):5.1(lactate); 4.2-4.4(—$OCH_2$—); 1.3-1.4(lactate).

EXAMPLE 3

Preparation of the Formula (I) Compound (1)

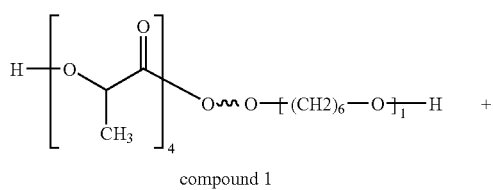

compound 1

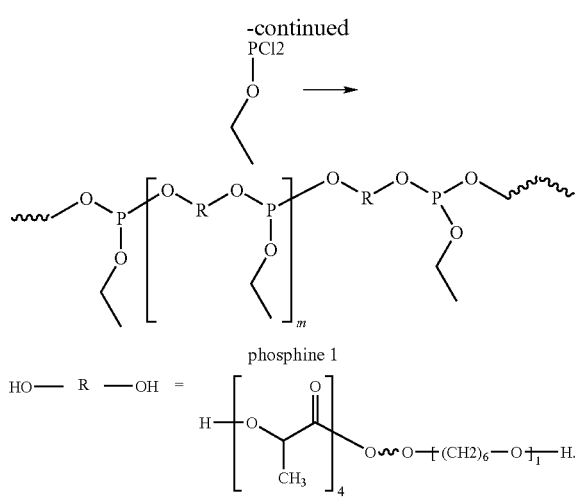

Formula (II) compound (compound 1) prepared by Example 1 was reacted with P(OEt)Cl$_2$ (molar ratio of 1:1) at 40° C. with diisopropyl ethylamine (catalyst) for 5 hours to prepare Formula (I) compound (phosphine 1).
$^1$HNMR(CDCl$_3$, ppm):5.1(lactate); 4.2-4.4(—OCH$_2$—); 1.4-1.5(—CH$_2$); 1.3-1.4(—CH$_3$).

EXAMPLE 4

Preparation of the Formula (I) Compound (2)

Formula (II) compound prepared by Example 2 was reacted with P(OEt)Cl$_2$ (molar ratio of 1:1) at 40° C. with diisopropyl ethylamine (catalyst) for 5 hours to prepare Formula (I) compound.
$^1$HNMR(CDCl$_3$, ppm):5.1(lactate); 4.2-4.4(—OCH$_2$—); 1.3-1.4(—CH$_3$).
$^{31}$PNMR(CDCl$_3$,ppm):139(phosphine).

EXAMPLE 5

Anti-pyrolysis Test for PLA Blended with Phosphine-based Polymer

Dried PLA and the Formula (I) compound (additive) prepared by Example 3 were blended in a twin screw extruder (screw diameter=30 mM, L/D=52, temperature=230° C., retention time=7 minutes). The molecular weight of the formed ester particle was analyzed with GPC, as shown in Table 1.

TABLE 1

| Additive amount (wt %) | PLA molecular weight (before heating) (g/mole) | PLA molecular weight (after heating) (g/mole) | Molecular weight ratio (Mw (after heating)/Mw (before heating)) |
|---|---|---|---|
| 0 | 211,320 | 126,792 | 65 |
| 0.1 | 211,320 | 166,942 | 80 |
| 1.0 | 211,320 | 181,735 | 86 |
| 5.0 | 211,320 | 175,395 | 83 |

The results indicate that the PLA blended with the phosphine-based polymer (additive) had a higher molecular weight than that of the conventional PLA after heating, with a molecular weight ratio (Mw(after heating)/Mw(before heating)) exceeding 80%.

EXAMPLE 6

Melt-blown Spinning Test for the PLA Blended with the Phosphine-based Polymer

Dried PLA and the Formula (I) compound (additive) prepared by Example 4 were blended and spun with melt-blown spinning at 230° C. The molecular weight of the formed melt-blown nonwoven was analyzed with GPC, as shown in Table 2.

TABLE 2

| Additive amount (wt %) | PLA molecular weight (before heating) (g/mole) | PLA molecular weight (after heating) (g/mole) | Molecular weight ratio (Mw (after heating)/Mw (before heating)) |
|---|---|---|---|
| 0 | 210,041 | 130,225 | 62 |
| 1.0 | 210,041 | 176,434 | 84 |
| 5.0 | 210,041 | 170,133 | 81 |

The results indicate that the PLA blended with phosphine-based polymer (additive) had a higher molecular weight than that of the conventional PLA after heating, with a molecular weight ratio (Mw(after heating)/Mw(before heating)) exceeding 80%. The melt-blown nonwoven had strength not less than 1.5 Kg/5 cm, fiber fineness not greater than 10 μm and a basis weight not less than 70 g/m$^2$.

EXAMPLE 7

Long Fiber Spinning Test for PLA Blended with Phosphine-based Polymer

Dried PLA and the Formula (I) compound (additive) prepared by Example 4 were blended and spun with a long fiber spinning (spinneret diameter=0.3 mM, temperature=230° C., retention time=7 minutes). The molecular weight of the formed fiber was analyzed with GPC, as shown in Table 3.

TABLE 3

| Additive amount (wt %) | PLA molecular weight (before heating) (g/mole) | PLA molecular weight (after heating) (g/mole) | Molecular weight ratio (Mw (after heating)/Mw (before heating)) |
|---|---|---|---|
| 0 | 210,450 | 134,688 | 64 |
| 1.0 | 210,450 | 174,673 | 83 |
| 5.0 | 210,450 | 172,569 | 82 |

The results indicate that the PLA blended with phosphine-based polymer (additive) had a higher molecular weight than that of the conventional PLA after heating, with a molecular weight ratio (Mw(after heating)/Mw(before heating)) exceeding 82%. After extending 1.5 times, the fiber had long fiber fineness of 1.5 dpf, strength of 3.1 g/d and extension of 30-40%.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A phosphine-based polymer having Formula (I):

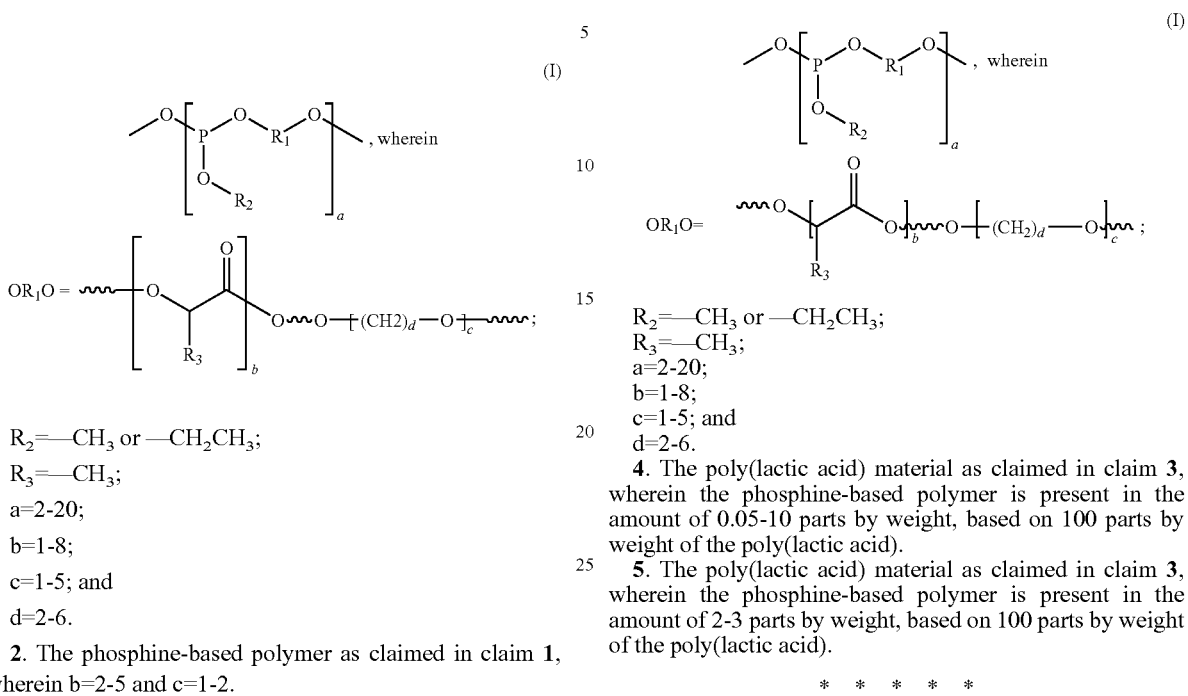

$R_2$=—$CH_3$ or —$CH_2CH_3$;
$R_3$=—$CH_3$;
a=2-20;
b=1-8;
c=1-5; and
d=2-6.

2. The phosphine-based polymer as claimed in claim 1, wherein b=2-5 and c=1-2.

3. A poly(lactic acid) material, comprising:
poly(lactic acid); and
a phosphine-based polymer having Formula (I):

$R_2$=—$CH_3$ or —$CH_2CH_3$;
$R_3$=—$CH_3$;
a=2-20;
b=1-8;
c=1-5; and
d=2-6.

4. The poly(lactic acid) material as claimed in claim 3, wherein the phosphine-based polymer is present in the amount of 0.05-10 parts by weight, based on 100 parts by weight of the poly(lactic acid).

5. The poly(lactic acid) material as claimed in claim 3, wherein the phosphine-based polymer is present in the amount of 2-3 parts by weight, based on 100 parts by weight of the poly(lactic acid).

* * * * *